United States Patent [19]

Davenport

[11] Patent Number: 4,684,014
[45] Date of Patent: Aug. 4, 1987

[54] IOL LOOP RETENTION PACKAGE AND METHOD

[75] Inventor: James M. Davenport, Laguna Niguel, Calif.

[73] Assignee: American Hospital Supply Corp., Evanston, Ill.

[21] Appl. No.: 806,666

[22] Filed: Dec. 9, 1985

[51] Int. Cl.⁴ .................. A45C 11/04; A61F 2/16
[52] U.S. Cl. ................... 206/5.1; 206/438; 623/6
[58] Field of Search ............. 623/6; 206/5.1, 438, 206/439, 485, 486, 6; 220/82 A

[56] References Cited

U.S. PATENT DOCUMENTS

| | | | |
|---|---|---|---|
| 4,113,088 | 9/1978 | Binkhorst | 206/210 |
| 4,149,279 | 4/1979 | Poler | 623/6 |
| 4,173,281 | 11/1979 | Trought | 206/5.1 |
| 4,205,747 | 6/1980 | Gilliam et al. | 206/5.1 |
| 4,257,521 | 3/1981 | Poler | 206/5.1 |
| 4,269,307 | 5/1981 | LaHaye | 206/5.1 |
| 4,326,306 | 4/1982 | Poler | 623/6 |
| 4,328,595 | 5/1982 | Sheets | 623/6 |
| 4,402,396 | 9/1983 | Graham | 206/5.1 |
| 4,418,431 | 12/1983 | Feaster | 623/6 |
| 4,423,809 | 1/1984 | Mazzocco | 206/5.1 |
| 4,437,194 | 3/1984 | Hahs | 623/6 |
| 4,463,457 | 8/1984 | Kelman | 623/6 |
| 4,508,216 | 4/1985 | Kelman | 206/5.1 |
| 4,543,673 | 10/1985 | Drake et al. | 623/6 |

OTHER PUBLICATIONS

"An Intraocular Lens Carrier", *American Medical Intra-ocular Implant Society Journal*, Osvaldo I. Lopez, M.D., et al., vol. 9, No. 4 (Fall 1983), pp. 477-479.

*Primary Examiner*—Ronald L. Frinks
*Attorney, Agent, or Firm*—Gordon L. Peterson

[57] ABSTRACT

An assembly comprising an intraocular lens and a lens case. The intraocular lens includes an optic and at least one fixation member attached to the optic, with the fixation member having a desired configuration. The lens case has an optic cavity for receiving the optic and a fixation member cavity for holding the fixation member in substantially the desired configuration.

16 Claims, 4 Drawing Figures

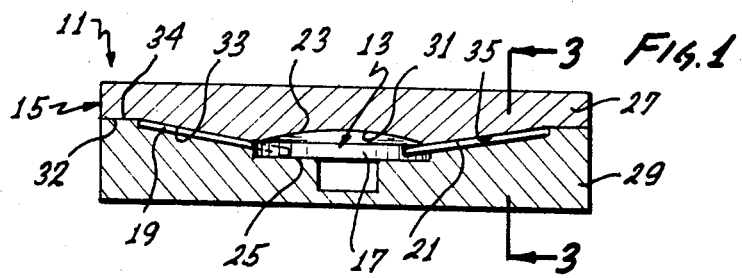
Fig.1
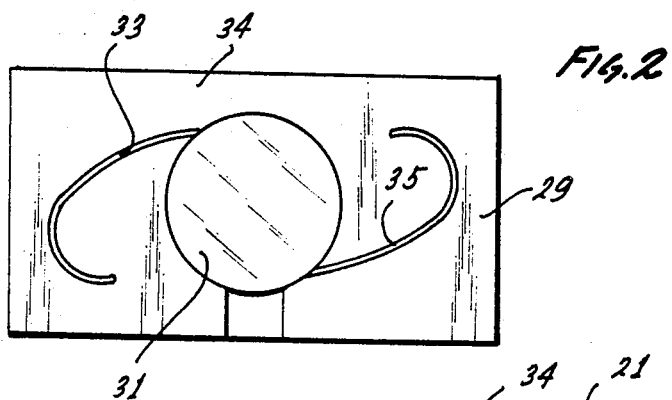
Fig.2
Fig.3
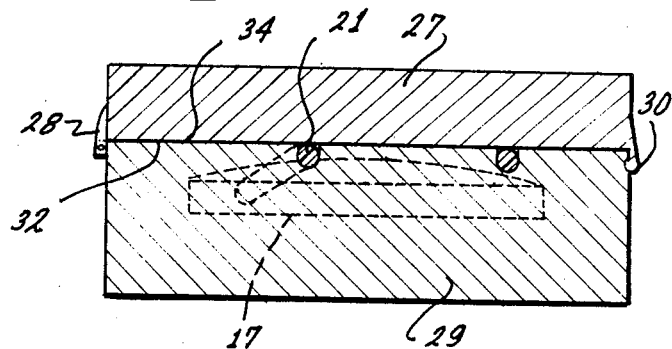
Fig.4

IOL LOOP RETENTION PACKAGE AND METHOD

BACKGROUND OF THE INVENTION

An intraocular lens (IOL) is commonly used to replace the natural lens of the human eye when the condition of the natural lens so warrants. An IOL typically comprises an optic and fixation members. The fixation members are used to retain the optic in the correct optical position within the eye.

The fixation members must be biocompatible, resilient and not degrade in the presence of active ocular tissue. This severely limits the materials available for use as fixation members. For example, polypropylene, polyamide and extruded polymethylmethacrylate (PMMA) are suitable materials for the fixation members. However, fixation members of these materials, and in particular polypropylene, even though permanently formed into the desired shape, tend to relax over a period of time toward another configuration, which may be their initial or preformed configuration. This makes it difficult to maintain accurate control over the configuration of the fixation members. This in turn may cause problems with the implanted IOL, such as decentration or improper vaulting of the optic.

SUMMARY OF THE INVENTION

This invention provides a method and apparatus which tend to assure that the fixation members will substantially retain their desired configuration. This can be accomplished by packaging the IOL in a lens case that holds the fixation members in substantially the desired configuration. This tends to assure that the fixation members will retain the desired configuration during shipment and storage. It has been found that maintaining the configuration of the fixation members during these periods is of greatest importance because, once implanted, the forces on the fixation members tend to limit the relaxation which they can undergo.

Although the lens case can take different forms, preferably it includes a container having an optic cavity for containing the optic and a fixation member cavity of substantially the desired configuration of the fixation member. The fixation member cavity receives the fixation member and retains it in substantially the desired configuration. Although the cavities can be formed in various different ways, such as by pins, it is preferred to use a groove for the fixation member cavity. Although it is not essential, preferably the optic cavity generally conforms to the configuration of the optic.

The lens case preferably substantially, completely encloses the IOL and is openable so that the IOL can be utilized. In a preferred construction, the lens case includes first and second case sections having confronting faces, and the optic cavity and the holding means for the fixation members are on at least one of the confronting faces.

According to one aspect of this invention, the fixation members are permanently preformed into the desired configuration and then packaged in a lens case which holds the fixation members in such desired configuration against any tendency that the fixation members may have to relax to another configuration. Alternatively, the lens case can be used to reshape the fixation members from an initial configuration into a desired configuration. In either event, the lens case ultimately holds the fixation members in the desired configuration and against relaxation or reshaping to another configuration.

If the lens case is to be used to change the configuration of the fixation members, the fixation members are preferably of a material which can be at least somewhat permanently reshaped in a process which includes heating the fixation members to a predetermined temperature. Such materials may be either thermoplastic or thermosetting. In any event, an IOL with resilient fixation members of a first configuration is placed into the lens case which resiliently forms the fixation members from the first configuration into a second configuration. The lens case and the IOL are then heated to at least about the predetermined temperature and held there for the necessary time to enable the permanent reshaping of the fixation member to the second configuration. In this instance, as well as those mentioned hereinabove, the lens case can then be used to ship and store the IOL and to retain the fixation members in the desired configuration.

When using the lens case to reshape the fixation members, it may be necessary or desirable to sterilize the case and IOL and to ultimately aerate the case and IOL. Both of these steps require heat, and if desired, the heat from these two steps can be used, in whole or in part, to heat the fixation member to the desired reshaping temperature.

The invention, together with additional features and advantages thereof, may best be understood by reference to the following description taken in connection with the accompanying illustrative drawing.

BRIEF DESCRIPTION OF THE DRAWING

FIG. 1 is a longitudinal sectional view through one form of lens case and IOL constructed in accordance with the teachings of this invention.

FIG. 2 is a top plan view of the lower case section with the IOL removed.

FIG. 3 is an enlarged sectional view taken generally along line 3—3 of FIG. 1.

FIG. 4 is a block diagram illustrating the basic steps in utilization of the lens case to reshape the fixation members.

DESCRIPTION OF THE PREFERRED EMBODIMENT

FIG. 1 shows an assembly 11 which comprises an IOL 13 and a lens case 15. Although the IOL 13 can be of various different configurations, in the embodiment illustrated, it includes an optic 17 and two resilient, polypropylene, generally J-shaped fixation members 19 and 21. Even though the fixation members are permanently set in the J-shaped configuration, they tend to relax or straighten somewhat over long periods of time. Although the fixation members 19 and 21 can be different from each other, in this embodiment, they are identical.

For example, the optic 17 has a cylindrical periphery, a convex anterior face 23 and a planar posterior face 25. The fixation members 19 and 21 are attached to the optic 13 adjacent the periphery of the optic using conventional techniques. Although various constructions are possible, in this embodiment, the fixation members 19 and 21 are vaulted anteriorly approximately 10 degrees.

Although the lens case 15 can be of different constructions, in this embodiment, it is in the form of a housing or container which includes case sections 27 and 29, both of which may be constructed of a suitable plastic material. The case sections 27 and 29 may be held together in the position shown in FIG. 1 in any suitable manner, such as by a hinge 28 and a suitable snap connector 30.

The lens case 15 has an optic cavity 31 and fixation member cavities 33 and 35 leading from the optic cavity. Although the cavities 31, 33 and 35 can be partially formed in confronting faces 32, 34 of the case sections 27 and 29, in this embodiment, the cavities 33 and 35 and the cylindrical portion of the cavity 31 are formed entirely in the confronting face 34 of the lower case section, and the cavities are closed by the upper case section 27. The lower case section 29 may have a groove 36 to facilitate removal of the IOL 13 from the case 15 in a known manner.

The optic cavity 31 is of substantially the same configuration as the optic 13. Similarly, the fixation member cavities 33 and 35 are of substantially the same configuration as the desired J-shaped configurations of the fixation members 19 and 21, respectively. In other words, the cavities 31, 33 and 35 are of the correct shape so that, if the lens case 15 were a mold, the casting produced by these cavities would substantially conform in size and shape to the IOL 13.

The optic cavity 31 is generally cylindrical and has a concave upper surface as viewed in FIG. 1, which in this embodiment, is formed in the confronting face 32 of the upper case section 27. Similarly, the fixation member cavities 33 and 35 are each in the form of an elongated groove or filament leading from the optic cavity. The fixation member cavities 33 are curved in accordance with the curvature of the fixation members 19 and 21, respectively.

Assuming that the IOL 13, and in particular the fixation members 19 and 21, are preformed from an initial configuration, which may be straight, into the desired J-shaped configuration, the IOL can be packaged in the lens case 15 as shown in FIG. 1, and there will be essentially no force or stress applied to the resilient fixation members 19 and 21 by the fixation member cavities 33 and 35. The optic 13 and the fixation members 19 and 21 are snugly retained in their respective cavities between the case sections 27 and 29, and the fixation member cavities 33 and 35 prevent the fixation members from relaxing out of the J-configuration during shipment and storage.

The lens case is next pouched, i.e., placed in a sterile bag (FIG. 4) and then run through ETO (ethylene oxide) sterilization by, for example, subjecting it to eythylene oxide for a period of six to eight hours at 130 to 135 degrees F. and then subjecting the lens case and the IOL 13 to aeration or degassing by blowing hot air across it at, for example, 130 degrees F. for a period which may be seven days in duration. The sterilization and aeration steps are known. It is immaterial whether or not the temperatures encountered by the fixation members 19 and 21 in the sterilizing and aerating steps are sufficient to cause loss of memory, i.e., loss of the permanent J-shape. If there is a loss in the permanent shape due to the heating of the thermoplastic fixation members 19 and 21, these fixation members will be reset to the desired J-shaped configuration by the J-shaped cavities 33 and 35 upon cooling of the fixation members.

The lens case 15 is then used to ship and store the IOL 13. Any tendency of the fixation members 19 and 21 to relax back to their initial shape, is resisted by the fixation member cavities 33 and 35. Consequently, when the IOL 13 is to be used, the configurations of the fixation members 19 and 21 are substantially in accordance with the desired configuration.

Alternatively, the IOL 13 may be constructed with the fixation members 19 and 21 in some configuration other than the desired J-shaped configuration illustrated. In this event, the IOL 13 is placed into the lens case 15, and the fixation members 19 and 21 are resiliently deformed by the cavities 33 and 35 from their intial configuration into the J-shaped configuration shown in FIG. 2. The lens case 15 is then closed by pivoting the case section 27 over the case section 29 and suitably securing it in position with the connector 30. The IOL 13 and the lens case 15 are then run through the pouching, sterilizing and aerating steps as described above.

Depending on the material employed for the fixation members 19 and 21, the temperature achieved in the sterilization and aeration steps may be sufficiently high and for a sufficient duration to enable the fixation members 19 and 21 to be permanently deformed into the desired J-shaped configuration of FIG. 2. If it is not, the temperature may be raised prior to, or subsequent to, sterilization and aeration. In this example, it is assumed that the temperature reached in the sterilizing and aerating steps is sufficient and is maintained for a sufficient duration to cause the thermoplastic fixation members 19 and 21 to, in effect, lose their memory so that, upon cooling, the fixation members are permanently set in the J-shaped configuration of the cavities 33 and 35.

Of course, the J-shaped configuration as shown in FIG. 2 for the fixation members 19 and 21 is only one of many possible shapes which may be the desired configuration for the fixation members.

Although an exemplary embodiment of the invention has been shown and described, many changes, modifications and substitutions may be made by one having ordinary skill in the art without necessarily departing from the spirit and scope of this invention.

I claim:

1. A lens case, comprising:
   a pair of first and second case sections having respective ones of a pair of first and second faces, which case sections are adapted to be placed together with the first and second faces confronting to define an optic cavity between the case sections in which to contain an intraocular lens having a fixation member mounted on the optic of the lens;
   which first and second case sections are adapted to be used as a packaging container for the lens;
   the first case section defining at least a first portion of the optic cavity in the first face in which to place the optic and a fixation member cavity in the first face in which to place the fixation member;
   the first portion of the optic cavity having a size and shape closely conforming to the size and shape of a first portion of the optic;
   the fixation member cavity extending from the first portion of the optic cavity along a curved path closely conforming to the desired fixation member configuration;
   which fixation member cavity defines a thin, elongated groove in which to insert a fixation member in the form of a thin filament that extends from the optic to a terminal end of the fixation member spaced apart from the optic, and which second case section is adapted to retain the optic and the fixation member within the optic and fixation member cavities securely when the case sections are placed together to inhibit relaxation of the fixation member from the desired fixation member configuration.

2. A lens case as defined in claim 1 wherein said optic cavity generally conforms to the configuration of the optic.

3. A lens case as defined in claim 1, wherein:
said fixation member cavity is generally in the shape of an elongated filament.

4. An assembly, comprising:
an intraocular lens including an optic and at least one filamentary fixation member attached to the optic, said fixation member extending from the optic to a terminal end of the fixation member spaced apart from the optic along a curved path in a desired fixation member configuration which the fixation member tends to lose over time;
an openable lens case containing the intraocular lens and having an optic cavity receiving the optic; and
means, including a thin groove in the lens case extending from the optic cavity along a curved path in the desired fixation member configuration, for holding the fixation member in the lens case in substantially said desired fixation member configuration.

5. An assembly as defined in claim 4 wherein said lens case includes first and second case sections having confronting faces and said optic cavity and said holding means are on at least one of said confronting faces.

6. An assembly as defined in claim 5 wherein said holding means includes a cavity of substantially said desired configuration receiving the fixation member therein and said optic cavity generally conforms to the shape of the optic.

7. A method comprising:
providing an intracular lens having an optic and at least one filamentary fixation member attached to the optic that extends from the optic along a curved path to a distal end of the fixation member in a desired member configuration, which fixation member is composed of a material which tends to relax toward another configuration which is different from said desired fixation member configuration;
using a packaging container in the form of an openable lens case having a pair of case sections defining an optic cavity in which to contain the optic of the lens and a fixation member cavity in which to contain the fixation member, which fixation member cavity is in the form of a thin elongated groove that extends from a first portion of the optic cavity along a curved path closely conforming to the desired fixation member configuration;
placing the optic in the optic cavity and the fixation member in the fixation member cavity; and
closing the lens case to thereby retain the intraocular lens between the case sections securely with the fixation member held in the desired fixation member configuration within the fixation member cavity, to thereby package the intraocular lens in a lens case which retains the fixation member in substantially said desired fixation member configuration whereby the tendency of the fixation member to relax toward said another configuration is reduced.

8. A method as defined in claim 7, further comprising:
heating the lens case sufficiently to plastically deform the fixation members to the desired fixation member configuration; and
allowing the lens case to cool to set the fixation members in the desired fixation member configuration.

9. A method, comprising:
providing an intraocular lens having an optic and at least one resilient filamentary fixation member attached to the optic that extends from the optic along a curved path to a distal end of the fixation member in a first configuration attached to the optic, which fixation member is composed of a material that can be at least somewhat permanently reshaped in a process which includes heating to a predetermined temperature;
using a packaging container in the form of an openable lens case having a pair of case sections defining an optic cavity in which to contain the optic of the lens and a fixation member cavity in which to contain the fixation member;
placing the optic in the optic cavity; and
resiliently deforming the fixation member to the desired fixation member configuration and placing the fixation member in the fixation member cavity;
thereby packaging the intraocular lens in the lens case which resiliently deforms the fixation member from said first configuration to the desired fixation member configuration;
heating the lens case with the intraocular lens therein to at least about said predetermined temperature for a sufficeint time to enable the fixation member to be permanently reshaped to said second configuration.

10. A method as defined in claim 9, including:
cooling the fixation member to fix it in said desired fixation member configuration.

11. A method as defined in claim 9, including:
shipping the intraocular lens in the lens case.

12. A method as defined in claim 9, wherein:
said step of heating is carried out to sterilize the intraocular lens and the lens case.

13. A method, comprising:
providing an intraocular lens having an optic and at least one resilient fixation member of a first configuration attached to the optic, said fixation member being of a material which can be at least somewhat permanently reshaped in a process which includes heating to a predetermined temperature;
packaging the intraocular lens in a lens case which resiliently deforms the fixation member from said first configuration to a second configuration;
heating the lens case with the intocular lens therein to at least about said predtermined temperature for a sufficient time to enable the fixation member to be permanently reshaped to said second configuration; and
ethylene oxide sterilizing of the lens case and the intraocular lens, subsequently aerating the lens case and the intraocular lens to remove the ethylene oxide and wherein said step of heating is carried out at least in part during said steps of sterilizing and aerating.

14. A method as defined in claim 13 including cooling the fixation member to fix it in said desired shape.

15. A method as defined in claim 13 including shipping the intraocular lens in the lens case.

16. A method as defined in claim 13 wherein said step of heating is carried out to sterilize the intracoular lens and the lens case.

* * * * *

UNITED STATES PATENT OFFICE
CERTIFICATE OF CORRECTION

Patent No. 4,684,014    Dated August 4, 1987

Inventor(s) James M. Davenport

It is certified that error appears in the above-identified patent and that said Letters Patent are hereby corrected as shown below:

Column 5, line 43 after "desired" insert -- fixation --.

Column 6, line 52 change "predtermined" to -- predetermined --.

Signed and Sealed this

Twelfth Day of January, 1988

Attest:

DONALD J. QUIGG

Attesting Officer    Commissioner of Patents and Trademarks